United States Patent
Drmosh et al.

(10) Patent No.: US 11,579,130 B2
(45) Date of Patent: Feb. 14, 2023

(54) ROOM TEMPERATURE UV-ACTIVATED HYDROGEN GAS SENSOR

(71) Applicant: KING FAHD UNIVERSITY OF PETROLEUM AND MINERALS, Dhahran (SA)

(72) Inventors: Qasem Ahmed Drmosh, Dhahran (SA); Zain Hassan Yamani, Dhahran (SA); Mohammad Kamal Hossain, Dhahran (SA); Mohammed Ashraf Gondal, Dhahran (SA); Abdulmajeed Hasan Hendi, Dhahran (SA); Redhwan Abdo Moqbel, Dhahran (SA)

(73) Assignee: KING FAHD UNIVERSITY OF PETROLEUM AND MINERALS, Dhahran (SA)

(*) Notice: Subject to any disclaimer, the term of this patent is extended or adjusted under 35 U.S.C. 154(b) by 521 days.

(21) Appl. No.: 16/725,455

(22) Filed: Dec. 23, 2019

(65) Prior Publication Data
US 2021/0190721 A1    Jun. 24, 2021

(51) Int. Cl.
*G01N 33/00* (2006.01)
*G01N 27/407* (2006.01)
*C01B 32/198* (2017.01)
*C01B 32/23* (2017.01)
*C02F 1/32* (2023.01)

(52) U.S. Cl.
CPC ......... *G01N 33/005* (2013.01); *C01B 32/198* (2017.08); *C01B 32/23* (2017.08); *C02F 1/32* (2013.01); *G01N 27/4074* (2013.01); *G01N 27/4075* (2013.01)

(58) Field of Classification Search
CPC .......... G01N 27/4074; G01N 27/4075; G01N 33/005; G01N 27/127; C01B 32/198; C01B 32/23
See application file for complete search history.

(56) References Cited

FOREIGN PATENT DOCUMENTS

| CN | 104034758 A | 9/2014 |
| CN | 105021655 B | 8/2017 |
| IN | 201641012578 A | 10/2017 |
| KR | 10-1430398 B1 | 9/2014 |
| KR | 10-1659320 B1 | 9/2016 |
| KR | 10-1736795 B1 | 5/2017 |

OTHER PUBLICATIONS

Drmosh et al. "UV-activated gold decorated rGO/ZnO heterostructured nanocomposite sensor for efficient room temperature H2 detection" (Year: 2019).*
Khosravi, et al. "Light-induced oxygen sensing using ZnO/GO based gas sensor" (Year: 2018).*

(Continued)

*Primary Examiner* — Benjamin R Schmitt
(74) *Attorney, Agent, or Firm* — Oblon, McClelland, Maier & Neustadt, L.L.P.

(57) ABSTRACT

A hydrogen sensor that efficiently detects hydrogen gas at room temperature comprising a gold decorated reduced graphene oxide/zinc oxide (Au/rGO/ZnO) heterostructured composite, methods for making this sensor and a method for sensitive room temperature detection of hydrogen using the sensor.

18 Claims, 28 Drawing Sheets

(56) References Cited

OTHER PUBLICATIONS

Yousef Khosravi, et al., "Light-induced oxygen sensing using ZnO/GO based gas sensor", Materials Science in Semiconductor Processing, vol. 85, Oct. 2018, pp. 9-14 (Abstract only).
Zain Ul Abideen, et al., "Sensing behavior to ppm-level gases and synergistic sensing mechanism in metal-functionalized rGO-loaded ZnO nanofibers", Sensors and Actuators B: Chemical, vol. 255, 2018, pp. 1884-1896.
Ruiqin Peng, et al., "Reduced graphene oxide wrapped Au@ZnO core-shell structure for highly selective triethylamine gas sensing application at a low temperature", Sensors and Actuators A: Physical, vol. 283, 2018, pp. 128-133.
Wen Chang Huang, et al., "Incorporation of carbon nanotube and graphene in ZnO nanorods-based hydrogen gas sensor", Ceramics International, vol. 44, Issue 11, Aug. 1, 2018, pp. 12308-12314 (Abstract only).
Q.A. Drmosh, et al., "UV-activated gold decorated rGO/ZnO heterostructured nanocomposite sensor for efficient room temperature $H_2$ detection", Sensors and Actuators B: Chemical, vol. 290, Jul. 1, 2019, pp. 666-675 (Abstract only).

\* cited by examiner

In air

In air

In H₂

ROOM TEMPERATURE UV-ACTIVATED HYDROGEN GAS SENSOR

STATEMENT REGARDING PRIOR DISCLOSURES BY THE INVENTOR OR A JOINT INVENTOR

Aspects of this technology are disclosed by Q. A. Drmosh, et al., Sensors and Actuators B: Chemical, Volume 290, Pages 666-67, 1 Jul. 2019 (available on line 30 Mar. 2019.

BACKGROUND OF THE INVENTION

Field of the Invention

The invention pertains to the fields of chemistry, clean fuels, and hydrogen gas sensors that operate at room temperature.

Description of Related Art

Hydrogen ($H_2$) has recently gained attention as a clean energy source substituting for fossil fuel. Unlike carbon-based fossil fuels hydrogen oxidizes (burns) in the presence of oxygen without producing carbon dioxide or carbon monoxide. However, hydrogen is flammable and potentially explosive when mixed with air at concentrations of 4 vol. % or more. Thus, there are serious concerns regarding its safe usage, transportation, and storage.

Many attempts have been made to develop $H_2$ gas sensing technology for accurate monitoring and detection of hydrogen gas for industrial and domestic applications. See J. L. Johnson, et al., *Hydrogen Sensing Using Pd Functionalized Multi-Layer Graphene Nanoribbon Networks*, Adv. Mater. 22 (2010) 4877-4880; and C.-M. Chang, et al., *Outstanding $H_2$ Sensing Performance of Pd Nanoparticle-Decorated ZnO Nanorod Arrays and the Temperature-Dependent Sensing Mechanisms*, ACS Appl. Mater. Interfaces 5 (2013) 135-143.

Metal oxide semiconductor nanostructures have drawn a significant interest in gas sensing applications because they are capable of detecting numerous gas species; Y. Liu, Jet al., *Pt nanoparticles functionalized 3D $SnO_2$ nanoflowers for gas sensor application*, Solid-State Electron. 130 (2017) 20-27; B. Gong et al., *UV irradiation-assisted ethanol detection operated by the gas sensor based on ZnO nanowires/optical fiber hybrid structure*, Sensors and Actuators B: Chem., 245 (2017) 821-827; S. Liang, et al., *Highly sensitive acetone gas sensor based on ultrafine α-$Fe_2O_3$ nanoparticles*, Sensors and Actuators B: Chem. 238 (2017) 923-927; S. Park, *Acetone gas detection using $TiO_2$ nanoparticles functionalized $In_2O_3$ nanowires for diagnosis of diabetes*, J. Alloys Compounds 696 (2017) 655-662; and S. S. Shendage et al., *Sensitive and selective $NO_2$ gas sensor based on $WO_3$ nanoplates*, Sensors and Actuators B, Chem. 240 (2017) 426-433.

Notably, zinc oxide (ZnO) nanostructures, which at room temperature have direct band gap energies of 3.3 eV and large exciting binding energies of 60 meV, have been investigated as gas sensing materials owing to a high specific surface area, high electron mobility, and good chemical and thermal stability; R. Kumar, et al., *Zinc Oxide Nanostructures for $NO_2$ Gas-Sensor Applications: A Review*, Nano-Micro Letters 7 (2015) 97-120. Among ZnO nanostructures, two dimensional (2D) ZnO nanoplates exhibit excellent gas sensing properties because of their high surface to volume ratios, high surface activities, and thickness of the depletion layer; C. Xiao, et al., *Synthesis of ZnO nanosheet arrays with exposed (100) facets for gas sensing applications*, Phys. Chem. Chem. Phys. 18 (2016) 325-330; and F. Fan, et al., *Facile synthesis and gas sensing properties of tubular hierarchical ZnO self-assembled by porous nanosheets*, Sensors and Actuators B: Chemical 215 (2015) 231-240.

However, ZnO thin films have not been widely used due to the low sensitivity, as well as low response and recovery time; Q. A. Drmosh, Z. H. Yamani, *Synthesis, characterization, and hydrogen gas sensing properties of AuNs-catalyzed ZnO sputtered thin films*, Applied Surface Science, 375 (2016) 57-64]

Moreover, unfortunately, efficient nanostructured ZnO-based sensors operate at elevated temperatures ranging from 300-500° C., which causes excessive power consumption and deterioration of sensor stability; R. Yoo, S. et al., *Highly sensitive gas sensor based on Al-doped ZnO nanoparticles for detection of dimethyl methylphosphonate as a chemical warfare agent simulant*, Sensors and Actuators B: chemical 221 (2015) 217-223; and H. S. Woo, et al., *Highly selective and sensitive xylene sensors using Ni-doped branched ZnO nanowire networks*, Sensors and Actuators B: Chemical 216 (2015) 358-366.

The low sensitivity of these sensors as well as their long response/recovery times at room temperature remain as unresolved problems; Chang et al. id. (2013); and Z. Zhang, et al., *Hydrogen gas sensor based on metal oxide nanoparticles decorated graphene transistor*, Nanoscale, 7 (2015) 10078-10084. The lower sensitivity of these sensors towards $H_2$ is attributed to the relatively inert surface state on the nanostructured ZnO surface for $H_2$ adsorption; W. An, et al., *Adsorption of $O_2$, $H_2$, CO, $NH_3$, and $NO_2$ on ZnO Nanotube: A Density Functional Theory Study*, J. Phys. Chem. C 112 (2008) 5747-5755; and Chang et al. id (2013).

A number of different techniques have been investigated for increasing the sensitivity of hydrogen gas sensors at various temperatures. These include surface modification with noble metals such as Pd, Pt, or Au; construction of metal oxide heterostructures such as $ZnO/SnO_2$, $ZnO/WO_3$, $TiO_2/WO_3$ and $TiO_2/SnO_2$; use of reduced graphene oxide. (rGO); as well as UV light activation. However, even though these approaches can enhance the sensing performance of nanostructured ZnO sensors, the operating temperature is typically reduced to about 200° C. which is significantly above room temperature (25° C.). Thus such high-temperature sensors still pose a big challenge for detecting gases in flammable and explosive environments; K. Anand, et al., *Hydrogen sensor based on graphene/ZnO nanocomposite*, Sensors and Actuators B: Chemical 195 (2014) 409-415; and N. D. Chinh, et al., *NO gas sensing kinetics at room temperature under UV light irradiation of $In_2O_3$ nanostructures*, Scientific Reports 6 (2016) 35066-35076.

There remains a need to reduce the operating temperature of hydrogen sensors to room temperature to provide safe sensing of flammable or explosive conditions in many environments as well as to provide lower power consumption and improved and easier integration of hydrogen sensors into electronic circuits.

In view of the limitations and problems with existing technologies, the inventors sought to develop a durable hydrogen gas sensor that efficiently and accurately detects hydrogen gas at room temperature.

BRIEF SUMMARY OF THE INVENTION

One aspect of the invention is directed to a hydrogen sensor that efficiently detects hydrogen gas at room temperature comprising, consisting essentially of, or consisting of a gold decorated reduced graphene oxide/zinc oxide (Au/rGO/ZnO) heterostructured composite and to methods for making this sensor.

Another aspect of the invention is a method for detecting hydrogen gas at room temperature using this sensor, optionally where UV irradiation is applied to the sensor.

The invention is also directed to a method for making the Au decorated rGO/ZnO nanocomposite by synthesizing ZnO nanorods hydrothermically, preparing GO by Hummer's method and producing a rGO/ZnO heterostructured composite by pulsed laser ablation followed by decorating this nanostructure with gold to produce a Au/rGO/ZnO heterostructured composite.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 4A: high resolution XPS spectra for Au 4f FIG. 4B: Zn 2p. FIG. 4C: O 1s. FIG. 4D: regions of Au/rGO/ZnO heterostructure. FIG. 4E: high resolution XPS spectra for C 1s regions of GO. FIG. 4F: Au/rGO/ZnO heterostructure.

DETAILED DESCRIPTION OF THE INVENTION

Figure 1A:
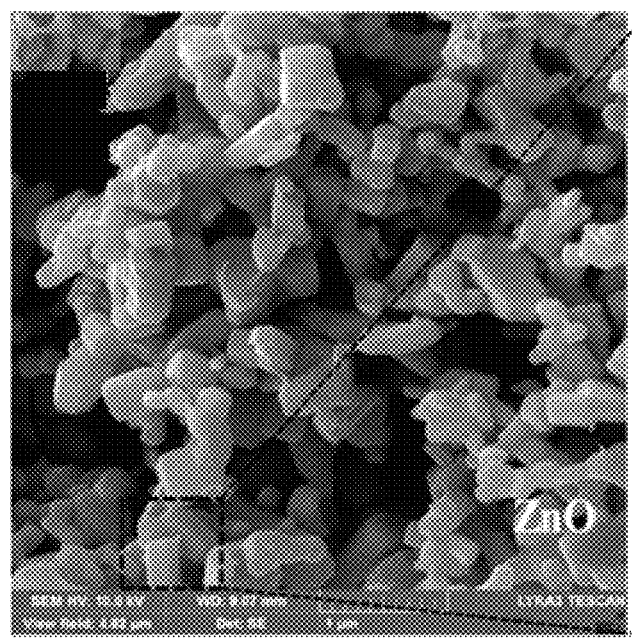
FIG. 1A depicts pristine ZnO by SEM micrography. The area within the lower left dashed square is enlarged and shown by FIG. 1B.

Non-limiting embodiments of the invention include, but are not limited to the following.

One aspect of the invention is directed to a heterostructured composite comprising reduced graphene oxide (rGO) and zinc oxide (ZnO) decorated with gold nanoparticles or with a thin gold film.

Typically, this composite comprises hexagonal sheets, but in some embodiments may contain rGO. These hexagonal sheets may have a diameter ranging from 500, 600, 700, 800-900 nm, preferably 573-860 nm, measured between opposing points of the hexagon, a length on each side of about 250, 300, 350, 400, 450-500 nm, preferably 301 to 451 nm, and a thickness ranging from 25, 50, 75 to 100 nm, preferably 50 to 74 nm. In other embodiments the hexagonal sheets have a diameter of about 680-752 nm, a length on each side of about 357-395 nm and a thickness of 59 to 65 nm.

This composition may comprise a sheet of rGO attached to hexagonal sheets of ZnO decorated with the Au nanoparticles or thin Au film.

A weight ratio of rGO to ZnO content of the heterostructured composition can range from 1.5:1 to 1:1.5, 1.4:1 to 1:1.4, 1.3:1 to 1:1.3, 1.2:1 to 1:1.2 or about 1:1. The amount of Au thin film or Au nanoparticles may range from 0.01, 0.02, 0.05, 0.1, 0.2, 0.5, 1, 2 or 5 wt % based on the weight of the entire composition including the rGO and ZnO. A thin Au film typically ranges from <1, 1, 2, 3, 4 or 5 nm in thickness, though greater thicknesses may be applied. Au nanoparticles may range in size from about <1, 1, 2, 3, 4, 5, 10, 20, 50 or >50 nm in average diameter. In a preferred embodiment, the Au thin film is applied as individual nanoparticles. In another embodiment, the Au thin film is about 10, 15, 20, 25 to 30 nm in thickness, preferably about 20 nm thick.

Another embodiment of the invention is a hydrogen sensor comprising the rGO/ZnO or Au/rGO/ZnO composites as disclosed herein. In the sensor, the heterostructured composite is typically bound to a substrate, such as a non-conductive substrate or to part of an electrode. The sensor comprises at least two electrodes configured to measure resistance, conductance, impedance or capacitance through the heterostructured composite. In a preferred embodiment, the electrodes are interdigitated electrodes (IDE) such as IDSs comprising gold or platinum. In another preferred embodiment, the sensor can detect at least 500 ppm of hydrogen at room temperature (25° C.) in ambient atmosphere. Such a sensor may also detect at least 500 ppm of hydrogen at room temperature (25° C.), wherein a relative difference between a first hydrogen concentration measurement and a second hydrogen concentration measurement is less than 1% or which has a repeatability of at least 95, 96, 97, 98, 99, 99.5, or 99.9%.

Another embodiment of the invention is directed to a method of detecting and/or quantifying hydrogen gas in a sample that comprises contacting the sensor as disclosed herein with a sample suspected of containing hydrogen, optionally, irradiating the sensor with UV light during said contacting, and measuring the decrease in sensor resistance, conductance, impedance, or capacitance of the sensor when in contact with the sample.

In a preferred embodiment, this method further comprises irradiating the sensor with UV light during said contacting. Any wavelength of UV light may be used that enhances the ability of the sensor to detect hydrogen compared to a method performed in the dark or in the absence of UV irradiation. UV light ranges in wavelength between 10, 20, 50, 100, 200, 300 and 400 nm. An appropriate or preferred wavelength may be selected by those skilled in the art. In some embodiments, this method is performed using a sample that is a gas, in another the sample is a liquid. Samples may be part of a fluid flow to which the sensor is exposed or may be ambient gas or liquid samples placed into a container or vessel containing the sensor.

In other embodiments of this method for detecting hydrogen the contacting of the sensor or part of the sensor detecting hydrogen, occurs at a temperature of 10, 15, 20, 25, 30, 40, 50, 60, 70, 80, 90, 100, 150, 200, 250, 300, 350, 400 or >400° C.

Another embodiment of the invention is directed to a method for making a heterostructured Au/rGO/ZnO composite decorated with gold nanoparticles or decorated with a thin gold film. The method comprises optionally preparing ZnO nanorods by a hydrothermal method; irradiating a mixture of graphene oxide (GO) and ZnO nanorods submerged in an aqueous medium with a UV laser for a time and under conditions effective to reduce the GO to graphene oxide (rGO), to exfoliate ZnO nanorods, and to anchor the ZnO nanorods on the rGO sheets to form the heterostructured ZnO/rGO composite, and depositing nanoparticles or a thin layer of Au on the heterostructured ZnO/rGO composite.

In one embodiment of this method, a hydrothermal method used to produce the ZnO nanorods. The hydrothermal method comprises heating an aqueous alcoholic (e.g., ethanolic) solution of zinc salt (e.g. zinc nitrate), inorganic base (e.g., sodium hydroxide), and organic base (e.g., a dialkyamine such as diethylamine) at pH in the range of 11, 12, 13, to 14 and filtering and drying the resulting ZnO nano-rods; irradiating the mixture of GO and ZnO with a laser having a wavelength of about 355 nm; and the depositing a thin layer of Au on a sheet of ZnO/rGO composite by magnetron sputtering.

According to one aspect, the present disclosure relates to a hydrogen gas sensor. The term "hydrogen gas sensor" as used in this disclosure refers to a gas sensor for detecting hydrogen gas and/or determining a concentration of hydrogen gas. In some embodiments the hydrogen gas sensor 200 (see FIGS. 8A-8D) has a substrate 220 and a thin film of the Au/rGO/ZnO heterostructured composite 222 deposited thereon, wherein an electrical resistance (or an electrical conductance) of the Au/rGO/ZnO thin film 222 varies when the hydrogen gas sensor 200 is subjected (e.g., contacted/exposed) to a fluid comprising hydrogen gas thereby adsorbing hydrogen gas molecules onto a surface of the thin film 222. By detecting the extent of variations of the electrical resistance, a concentration of hydrogen gas may be determined. FIGS. 8A, 8B, 8C and 8D schematically represent the hydrogen gas sensor 200 with the substrate 220 and the thin film of Au/rGO/ZnO heterostructured composite 222 deposited thereon. In some embodiments, the hydrogen gas may be present in a fluid stream. In other embodiments, the sample may be taken from the environment under ambient conditions.

As used herein, the "substrate" is utilized to support the thin film of Au/rGO/ZnO heterostructured composite 222. The substrate 220 may be a glass substrate, a sapphire substrate, a quartz substrate, a magnesium oxide single crystal substrate, a ceramic substrate, an alumina substrate, a silicon substrate (e.g. silicon wafer or silicon oxide), a silicon nitride substrate, etc. The substrate 220 may have a thickness of 0.05-10 mm, preferably 0.1-5 mm, preferably 0.2-3 mm, although the thickness of the substrate 220 is not limited to these ranges and substrates with thicknesses outside of these ranges may also be used. In one embodiment a dispersion of the rGO/ZnO particles is applied by brushing onto an electrode substrate such to Pt interdigitated electrodes (IDE).

The "thin film" as used in the term "thin film of Au/rGO/ZnO heterostructured composite" refers to a film with a thickness of no more than 1, 2, 3, 4 or 5 µm, preferably in the range of 10 to 1,000 nm. In view of that, the hydrogen gas sensor 200 preferably does not contain thick films of the heterostructured nanocomposite, wherein the term "thick film" refers to a film with a thickness of greater than 5, 10 or 15 μm. Typically a film of rGO/ZnO is applied to a substrate and then decorated with Au. In some embodiments, the film may be decorated with another noble metal such as Ag, Ir, Os, Pt, Pd, Rh, or Ru. In some embodiments, the thin film may comprise rGO/ZnO without Au or other metal decoration.

ZnO nanorods have a direct bandgap energy of 3.37 eV and have an excitation binding energy of 60 meV. ZnO nanorods may be synthesized using methods known in the art, preferably by a hydrothermal method (as described herein). These methods include, but are not limited to those described by Wei, et al., Materials Sci. Engin. 393:8-82 (2005); Worasawat, et al., Materials Today Proc. 5(5): 10964-10969 (2018); or Eldalati, K, et al., Mat. Res. Bull 74:374-379 (2016), each of which is incorporated by reference.

Hummers' method is a chemical process that can be used to generate graphite (graphene) oxide through the addition of potassium permanganate to a solution of graphite, sodium nitrate, and sulfuric acid. Graphene oxide is effectively a by-product of this oxidization as when the oxidizing agents react with graphite, the interplanar spacing between the layers of graphite is increased. The completely or partially oxidized compound can then be dispersed in a base solution such as water, and graphene oxide is then produced. In order to turn graphite oxide into graphene oxide, a few methods are possible. The most common techniques are by using sonication, stirring, or a combination of the two. Sonication can be a very time-efficient way of exfoliating graphite oxide, and it is extremely successful at exfoliating graphene (almost to levels of full exfoliation), but it can also heavily damage the graphene flakes, reducing them in surface size from microns to nanometers, and also produces a wide variety of reduced graphene oxide platelet sizes. Mechanically stirring is a much less heavy-handed approach, but can take much longer to accomplish. Other chemical, thermal or electrochemical procedures may be used to produce reduced graphene oxide. These include treating GO with hydrazine hydrate and maintaining the solution at 100 for 24 hours; exposing GO to hydrogen plasma for a few seconds; exposing GO to another form of strong pulse light, such as those produced by xenon flashtubes; and heating GO in distilled water at varying degrees for different lengths of time.

Figure 7A:
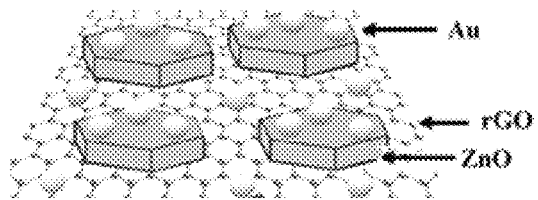
FIG. 7A. illustrates gas sensing mechanism of Au/rGO/ZnO sensor in air.
Figure 7B:
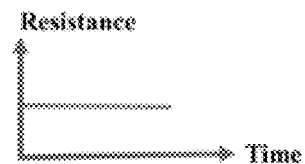
FIG. 7B depicts resistance of sensor of FIG. 7A.
Figure 7C:
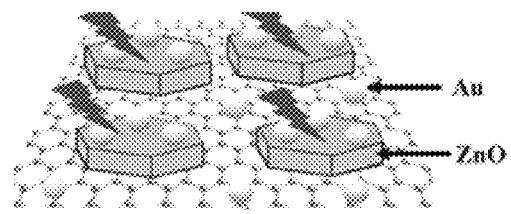
FIG. 7C illustrates gas sensing mechanism of Au/rGO/ZnO sensor in air with UV light.

The deposition of Au includes, optionally as a first step, depositing Au particles or film on the rGO/ZnO heterostructured composite on a substrate. The Au thin film may be deposited on the substrate by various methods know to those skilled in the art, for instance, sputtering, e.g. magnetron sputtering, electron beam deposition, chemical vapor deposition, wet deposition, etc. In a preferred embodiment, an Au film or particles of Au are deposited by magnetron sputtering at a power of 20, 30 to 40 W for a deposition time of about 20, 30, 40, 50 to 60 secs. A sputtering chamber can be evacuated to a pressure of less than $3.5\times10^{-6}$ Torr, preferably less than $3.0\times10^{-6}$ Torr, filled with an inert gas, preferably argon with a purity of 99.9% or preferably a purity of 99.999%, wherein the pressure of the sputtering chamber is raised to at least $5.0\times10^{-6}$ Torr, preferably at least $5.3\times10^{-6}$ Torr, but no more than $6.0\times10^{-6}$ Torr. A partial pressure of the inert gas may preferably be maintained in the range of 0.5-10 mTorr, preferably 1-5 mTorr in the sputtering chamber during sputtering. A sputtering power may set to a value in the range of 50, 100, 150, 200, 250, 300, 350, 400, 450 to 500 W, preferably 100 to 400 W. The Au nanoparticles may have an average particle size of less than 200 nm, preferably less than 100 nm, preferably 5 to 80 nm, preferably 10 to 50 nm, more preferably 20 to 40 nm. The metallic nanoparticles may have similar rounded shapes, or may have various shapes including, without limitation, spherical, elliptical, cubical, hexagonal, pyramidal, conical, and/or irregular shapes. A thickness of the Au thin film, particles or decoration after the sputtering may preferably be in the range from about 1 nm to 1 μm, preferably 20 to 900 nm. Preferably, as shown by FIGS. 7A and 7C, the Au decoration does not cover the entire rGO/ZnO heterostructured composite applied on a substrate.

In some embodiments, the Au/rGO/ZnO heterostructure will be characterized by hexagonal structures about 573-860 nm in diameter, about 301 to 451 nm in length of each side, and about 50 to 74 nm in thickness. In another embodiment the Au/rGO/ZnO heterostructured composite will be characterized by hexagonal structures about 644-788 nm in diameter, about 338 to 414 nm in length of each side, and about 56 to 68 nm in thickness. In another embodiment the Au/rGO/ZnO will be characterized by hexagonal structures about 680-752 nm in diameter, about 357 to 395 nm in length of each side, and about 59 to 65 nm in thickness. One example of these structures is shown by FIG. 1J.

In addition to the heterostructured composite material disclosed herein a sensor may comprise a non-conducting substrate comprising two electrodes each of which is in contact with the heterostructured composite material, e.g., indirect physical and electrical contact or indirect electrical contact through another structure or material, so as to form a circuit through which current may flow from one electrode through the composite to the other electrode. This circuit typically contains a battery or other source of electrical current and a device for measuring resistance, conductance, impedance or capacitance, such as an analog or digital meter, when the sensor is in contact with a sample, such as a sample containing air or a mixture containing hydrogen. The circuit may comprise an interdigitated electrode coated with the heterostructured composite disclosed herein, for example, it may contain an interdigitated gold or platinum electrode coated with the heterostructure Au/rGO/ZnO composite disclosed herein.

In some embodiments the sensor may contain other components such as a chamber containing a sample or a contact point between the heterostructure Au/rGO/ZnO composite hydrogen-sensing material and a gaseous or liquid fluid stream. It may contain a heater or cooler to control the temperature during detection of hydrogen in a sample. The sensor may be linked to other external elements or electronic circuits such as a processor or display. It may contain a display device which indicates a change in resistance, conductance, impedance or capacitance or the amount of hydrogen in a sample based on calibration of these changes with hydrogen content in a sample.

In a method of determining a concentration of hydrogen (preferably hydrogen gas) in a sample or fluid stream with the hydrogen gas sensor, the sensor may be configured and used to detect hydrogen in a sample, such as a sample of ambient air or gas contained within a test chamber.

It may also be configured to detect hydrogen in a fluid stream which is preferably a gaseous stream that contains hydrogen gas and one or more of water vapor, carbon dioxide, ammonia, butane, pentane, butene, pentene, and so forth. Alternatively, the fluid stream may be a liquid stream, e.g. tap water, seawater, wastewater, or water from a river, a lake, a pond, etc. with infused in or In some embodiments, the concentration of hydrogen in the fluid stream may be within the range of 50 to 1,500 ppm, preferably 50 to 1,400 ppm. The concentration of hydrogen in the fluid stream is not limited thereto, and the concentration of hydrogen (or hydrogen gas) outside of these preferable ranges can also be determined with the hydrogen gas sensor. For example, in some embodiments, the hydrogen gas sensor may determine the concentration of hydrogen gas of at least 1 ppm, preferably at least 5 ppm, preferably at least 10 ppm. The hydrogen gas sensor may have a detection limit (lowest detectable concentration of hydrogen gas) of 1 to 1,000 ppb, preferably 5 to 500 ppb. The term "detection limit" as used herein, refers to the lowest concentration value detectable by the hydrogen gas sensor.

According to the method, in a first step the fluid stream is contacted with the hydrogen gas sensor (i.e. with the Au/rGO/ZnO nanostructured thin film of the hydrogen gas sensor). In some embodiments, the fluid stream is a liquid stream, wherein the hydrogen gas sensor is submerged (or partially submerging) therein. In some preferred embodiments, the fluid stream is a gaseous stream, which is passed over the hydrogen gas sensor. Preferably, the fluid stream may have a temperature 10 to 40° C., most preferably about room temperature, during contacting with the hydrogen gas sensor; and therefore, the concentration of hydrogen (or hydrogen gas) in the fluid stream is preferably determined at these preferable temperature ranges.

Once the fluid stream is contacted with the hydrogen gas sensor, the electrical resistance of the Au/rGO/ZnO nanostructured thin film varies, as described previously. Then, a response factor of the hydrogen gas sensor is measured. The response factor of the hydrogen gas sensor refers to a difference in an electrical resistance across the Au/rGO/ZnO nanostructured thin film during contacting with the fluid stream relative to prior to the contacting, which may be measured with the following equation (I):

$$\text{Response factor}(\%) = \frac{R_0 - R_g}{R_0} \times 100 \qquad (I)$$

wherein $R_0$ (initial electrical resistance) is the electrical resistance of the hydrogen gas sensor in air, and $R_g$ is the electrical resistance of the hydrogen gas sensor after contacting with the fluid stream. Each of $R_0$ and/or $R_g$ may be independently measured by a device known to those skilled in the art, e.g. an ohm-meter, an avometer, etc.

Once the response factor of a fluid stream is measured, the concentration of hydrogen (or hydrogen gas) may further be determined in the fluid stream based on the response factor. The concentration of hydrogen (or hydrogen gas) may be determined from the response factor via a calibration curve that correlates the response factor to the concentration of hydrogen (or hydrogen gas). For example, in some embodiments, the response factor is non-linearly correlated to the concentration of hydrogen (or hydrogen gas), and the calibration curve may have a general formula as represented by equation (II):

$$[H_2] = A*RF^2 + B*RF + C \qquad (II)$$

wherein "$[H_2]$" represents the concentration of hydrogen (or hydrogen gas) (in ppm), "RF" is the response factor, "A" is a first constant value in the range of 0.001 to 1,000, preferably 0.005 to 900, "B" is a second constant value in the range of 0.001 to 1,000, preferably 0.005 to 900, and "C" is a third constant value in the range of 0.001 to 1,000, preferably 0.005 to 900.

In one embodiment, the concentration of hydrogen gas in the fluid stream is in the range of 0.1 to 1,500 ppm, preferably 60 to 1,400 ppm, preferably 70 to 1,300 ppm, wherein the response factor is in the range of 10% to 60%, preferably 12% to 55%.

In one embodiment, the fluid stream is a gaseous stream that includes hydrogen gas and at least one compound selected from the group consisting of ammonia, butane, pentane, butene, pentene, and carbon dioxide, wherein a hydrogen selectivity of the hydrogen gas sensor is at least 80% by mole. As used herein, the term "hydrogen selectivity" refers to a ratio of a number of moles of the hydrogen gas that are adsorbed onto the Au/rGO/ZnO heterostructured thin film relative to the total number of moles that are adsorbed onto the thin film. For example, the hydrogen selectivity of the 80% by mole refers to an embodiment wherein 80% of all species that are adsorbed onto the thin film is hydrogen. The hydrogen selectivity of the hydrogen gas sensor 200 may be related to the specific surface area and the concentration of oxygen vacancies of the thin film. The hydrogen selectivity of the hydrogen gas sensor 200 for a fluid stream that includes ammonia, methane, butane, oxygen, and carbon dioxide is shown in FIG. 6D.

In some embodiments, the method has a repeatability of at least 95, 96, 97, 98, 99%, preferably at least 99.5%. The term "repeatability" as used herein refers to a relative difference between a first hydrogen concentration measurement and a second hydrogen concentration measurement, wherein the first and the second hydrogen concentration measurements are conducted at substantially the same conditions (i.e. temperature, pressure, composition of the fluid stream, etc.).

Preferably, the hydrogen gas sensor does not substantially age over time. The term "age" as used herein refers to degradation in properties of the hydrogen gas sensor over an extended period of time, e.g., at least two year, preferably more than two years. These properties may include detection limit, response time, repeatability, etc. For example, in some preferred embodiments, the hydrogen gas sensor is maintained for at least two years, preferably at least three years (for example at room temperature, i.e. 20 to 25° C., and atmospheric pressures, i.e. around 1 atm, in an inert atmosphere, e.g. argon), wherein a repeatability of determining the concentration of hydrogen gas using the hydrogen gas sensor is at least 95, 96, 97, 98, 99%, preferably at least 99.5%.

The examples below are intended to further illustrate protocols for the hydrogen gas sensor and methods of fabricating and using thereof, and are not intended to limit the scope of the claims.

EXAMPLES 2-1 Synthesis of ZnO Nanorods

ZnO nanorods were fabricated using a hydrothermal method. In a typical synthesis process, 2.97 g of zinc nitrate hexahydrate and 4 g of sodium hydroxide were dissolved in deionized water. About 3 mL of this solution was mixed with 5 mL of deionized water, 30 mL of ethanol, and 10 mL of diethylamine. The obtained solution was then sonicated for about 30 min. The pH of the solution was 13 before being transferred to Teflon-lined autoclaves. The hydrothermal treatment was carried out at 190° C. for 1 h. The product of white ZnO nanorods was collected, washed with ethanol and deionized water several times and dried at 70° C. for 24 h.

Synthesis of GO

Graphene oxide (GO) was fabricated using a modified Hummer's method, details of which are incorporated by reference to W. S. Hummers, R. E. Offeman, *Preparation of graphitic oxide*, J. Am. Chem. Soc. 80 (1958) 1339-1339 and to Q. A. Drmosh et al., *A novel approach to fabricating a ternary rGO/ZnO/Pt system for high-performance hydrogen sensor at low operating temperatures*, Applied surface Science 464 (2019) 616-626—incorporated herein by reference in its entirety.

In brief, 6 g of graphite, 3 g sodium nitrate, and 120 mL of sulfuric acid were mixed and stirred in an ice bath for 15 min. Next, 12 g of potassium permanganate was added gradually with continuous stirring to maintain the temperature of the mixture around 280 K. The suspension was then heated up at 305° K for 30 min. Afterwards, 20 mL of 5% $H_2O_2$ was added to the mixture to destroy the excess of permanganate. Finally, the obtained solution was repeatedly centrifuged and rinsed with 5% HCl solution as well as deionized water and then dried at 60° C.

Synthesis of Au/rGO/ZnO

The fabrication of the Au/rGO/ZnO heterostructured composite was performed using a two-step process. rGO/ZnO nanocomposite was prepared by focusing an intense pulsed UV laser beam (355 nm, 10 Hz, 8 ns) onto a 1.2% Go and ZnO nanorods that are submerged in water for 30 min. Details of this procedure are incorporated by reference to Q. A. Drmosh, et al., *Room-temperature detection of hydrogen by platinum-decorated tin oxide thin films augmented by heat-treatment*, Vacuum 156 (2018) pp. 68-77.

During the ablation process, the GO was substantially completely reduced to rGO and the ZnO nanorods were exfoliated and anchored on the rGO sheets to form 2D rGO/ZnO nanocomposite.

To investigate the gas sensing properties of samples, the fine powder of ZnO nanorods, and rGO/ZnO nanocomposite were dispersed in DI water through ultrasonication and 20 µL of dispersion was deposited onto the Pt interdigitated electrodes (IDE) using brushing method and dried in a hot vacuum oven at 100° C.

Finally, ultra-thin layer of Au was deposited on rGO/ZnO film using DC magnetron sputtering at RT with a power of 30 W and a deposition time of 40 s.

Characterization of Materials

The X-ray diffraction (XRD) analyses were acquired using a Rigaku MiniFlex X-ray diffractometer operating with Cu Kα radiation (λ=0.154178 nm) at 40 mA and 40 kV. The morphology of the fabricated materials was characterized by field emission scanning electron microscope (FE-SEM; Tescan Lyra-3). The surface contents were analyzed by X-ray Photoelectron Spectroscopy (XPS, ESCALAB250Xi, Thermo Fisher Scientific) using Mg Kα X-ray source. FTIR spectra were recorded using Nicolet iS50 FTIR spectrometer while Raman measurements were recorded using a Raman Thermo Fisher Scientific operating with 455 nm laser, 0.6 mm, and 4 mW at room temperature. The ultraviolet-visible (UV-Vis) spectra of the fabricated materials were recorded by double beam UV/Vis spectrophotometer (Jasco V-570) over the wavelength range of 200-700 nm.

Gas-Sensing Measurements

A schematic illustration of the gas sensing setup and details of this procedure are described by and incorporated by reference to Q. A. Drmosh, et al., *Gold nanoparticles incorporated $SnO_2$ thin film: highly responsive and selective detection of $NO_2$ at room temperature*, Materials Letters 214 (2018) 283-286—incorporated herein by reference in its entirety. The gas sensing measurements were carried out on a gas sensing test chamber called Linkham stage (HFS600E-PB4, Linkham Scientific Instruments). Nitrogen was used as the carrier gas and the flow rate of nitrogen and nitrogen/hydrogen mixture in the Linkham chamber was kept constant at 100 standard cubic centimeter per minute (SCCM) during the measurements to measure the sensing behavior of different hydrogen concentrations under the same conditions. The mixed gas flow was controlled using mass flow controller through an external power hub supply. The DC resistance of the sensor was calculated by an Agilent semiconductor device analyzer (SDA) in the dark and under UV irradiation at temperature range from RT to 450° C. Lumen Dynamics Omnicire series 2000 at 2 W/cm² was utilized as UV irradiation light source for testing the sensing properties of the fabricated sensors under light irradiation.

The response magnitude of the sensors was defined as $$\text{Response}(\%) = \frac{R_0 - R_g}{R_g} \times 100$$

where $R_o$ and $R_g$ are the resistance of sensor in the absence and the presence of $H_2$ gas, respectively.

Extended surface area, one of the key properties of nanostructured materials, is relevant to use of a material in a gas sensing application. Therefore, the inventors determined the morphology of the as-fabricated and as-modified specimens. FIGS. 1A-1J reveal and compare topographic conformations of ZnO and modified ZnO nanomaterials disclosed herein.

Figures 1B, 1C:
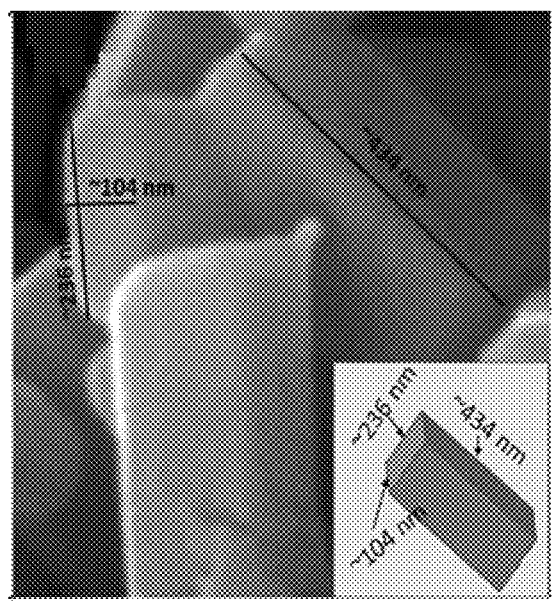
FIG. 1B provides an enlarged view of pristine ZnO by SEM micrography.
FIG. 1C (inset to FIG. 1B) provides an illustration representing typical dimensions of as-synthesized ZnO nanostructure (FIG. 1C) showing dimensions of 104, 236, and 434 nm.

SEM micrography of elongated ZnO nanoblocks is shown by FIG. 1A confirmed a wide variety of dimensions of the same. A magnified 700×700 nm area (dashed square in lower left corner) of the ZnO sample is shown in FIG. 1B. Typical dimensions of length, width and breadth were estimated to be 434, 104 and 236 nm respectively and are shown by the solid black lines in FIG. 1B. Further corresponding dimensions are clarified by the diagram shown by the inset of FIG. 1C. As explained above in the experimental section, treated ZnO nanoblocks were found to be very thin nanosheets of ZnO as confirmed by SEM observations.

Figures 1D, 1E:
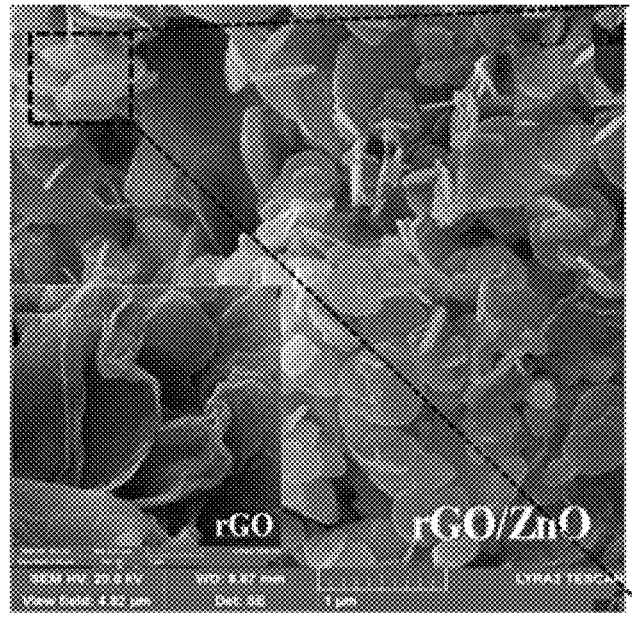
FIG. 1D (lower left inset to FIG. 1E) depicts an rGO nanostructure for comparison to rGO/ZnO nanostructure shown in FIGS. 1E-1F.
FIG. 1E is an SEM micrograph of rGO/ZnO structure. The area in the upper left dashed square is enlarged and shown by FIG. 1F.
Figures 1F, 1G:
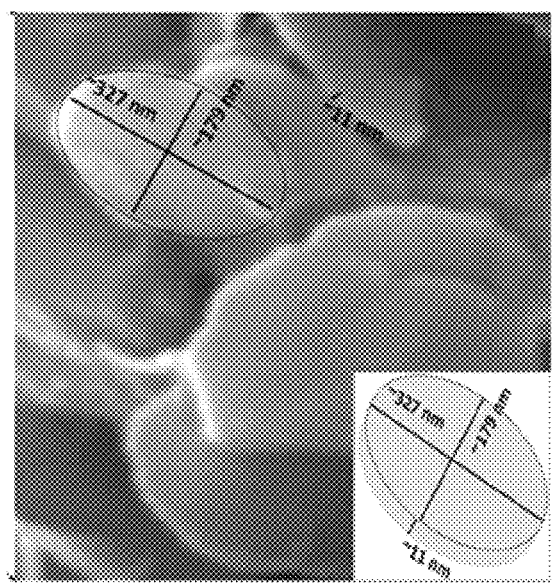
FIG. 1F provides an enlarged view of the rGO/ZnO structure.
FIG. 1G (lower right inset to FIG. 1F) provides an illustration representing typical dimensions of as-synthesized rGO/ZnO nanostructure showing dimensions of 11, 179 and 327 nm.

SEM micrography of raw rGO material is shown by FIG. 1D which is inset into larger FIG. 1E which shows the SEM micrograph of rGO/ZnO nanosheets. It is noteworthy that most of the nanosheets were found to be very thin and in oval shapes. A wide variety of dimensions of the same was observed in SEM observations. A 700×700 nm magnified area (dashed square in upper left corner of FIG. 1E), is shown by FIG. 1F. Typical dimensions of major axis, minor axis and thickness as estimated to be 327, 179 and 11 nm respectively was shown by solid blacklines in FIG. 1F. Further corresponding dimensions are clarified by the diagram as shown in inset of FIG. 1G.

Figure 1H:
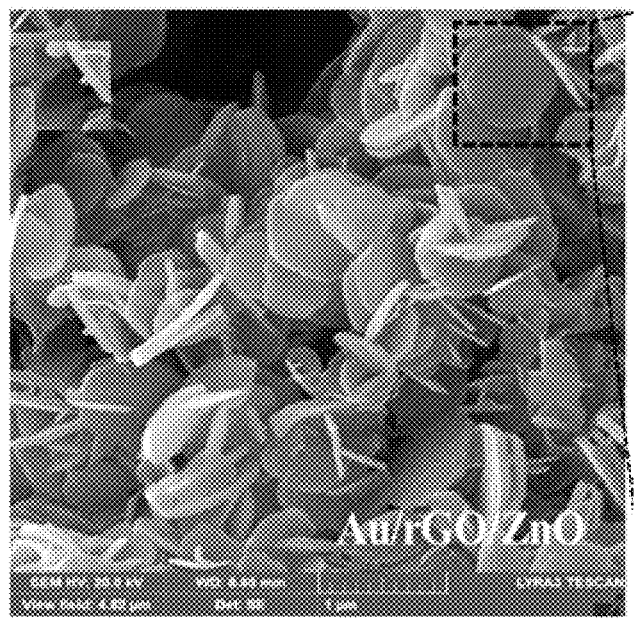
FIG. 1H shows an SEM micrograph of Au/rGO/ZnO. The area in the upper right dashed square is enlarged and shown by FIG. 1I.
Figures 1I, 1J:
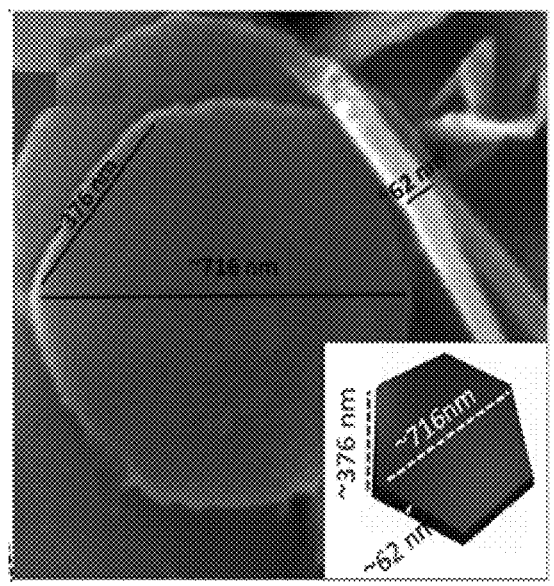
FIG. 1I provides an enlarged view of the Au/rGO/ZnO nanostructure.
FIG. 1J (inset to FIG. 1I) provides an illustration representing typical dimensions of as-synthesized Au/rGO/ZnO nanostructure showing dimensions of 62, 376, and 716 nm.

Further Au treatment of as-such ZnO nanosheets provided exciting nanostructures of ZnO shown by FIGS. 1H and 1I. This treatment turned the ultrathin ZnO nanosheets turned into thicker hexagonal nanosheets. Likewise, a wide variety of dimensions of the same was observed in SEM observations. A magnified 1000×1000 nm area (square dashed box in upper right corner of FIG. 1H) is shown by FIG. 1I. Typical dimensions of long diagonal, edge and thickness of hexagonal nanosheets as estimated to be 716, 376 and 11 nm respectively as shown by solid blacklines in FIG. 1I. Further corresponding dimensions are shown by the diagram sin inset of FIG. 1J.

Figure 2A:
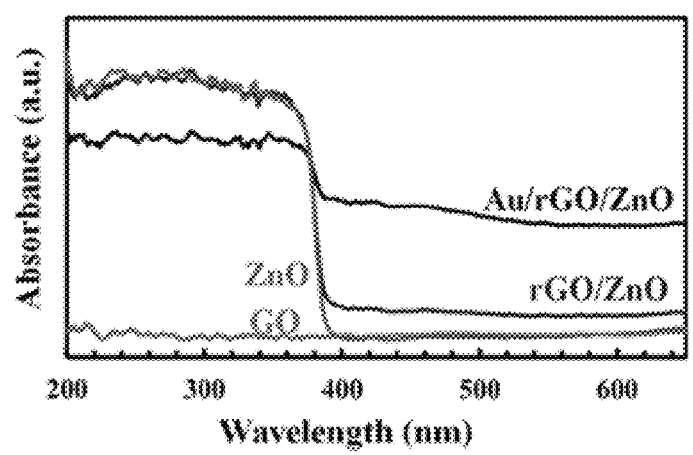
FIG. 2A shows the UV-vis absorption spectroscopy of pristine ZnO, rGO/ZnO and Au/rGO/ZnO nanostructures.
Figure 2B:
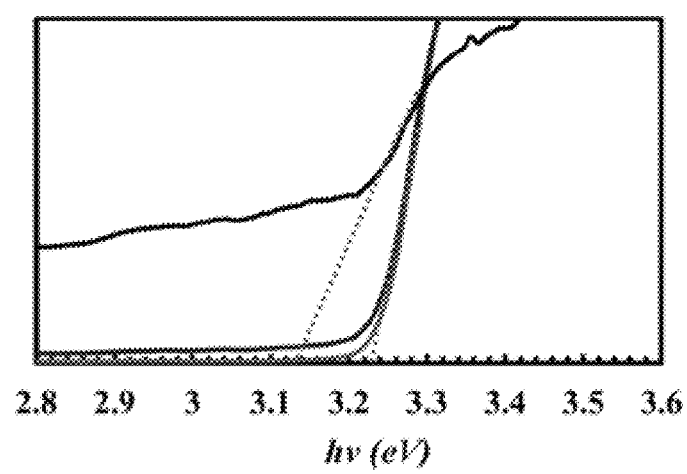
FIG. 2B shows a Tauc plot of pristine ZnO, rGO/ZnO and Au/rGO/ZnO nanostructures.

FIG. 2A shows UV-vis absorption of ZnO and ZnO incorporated rGO and rGO/gold. A clear band at 382 nm for ZnO and ZnO incorporated rGO was observed whereas addition shoulder peak at 460 nm in presence of gold was visible. The additional peak was found to be very weak, as the gold was used as catalyst to obtained nanostructures of ZnO incorporated rGO. A Tauc plot for ZnO and ZnO incorporated rGO and rGO/gold was derived and optical band gap of 382 nm (3.24 eV) was obtained for Zn and ZnO incorporated rGO as shown in FIG. 2B. In presence of gold ZnO incorporated rGO nanostructures' optical band gap was found to be slight shifted to 395 nm (3.14 eV).

Figure 2C:
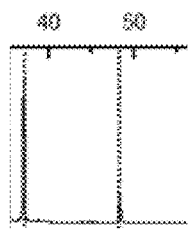
FIG. 2C shows X-ray diffraction patterns of pristine ZnO, rGO/ZnO and Au/rGO/ZnO nanostructures.

The synthesized ZnO and ZnO incorporated rGO and rGO/gold was reconfirmed by X-ray diffraction analysis as shown in FIG. 2C. As for GO samples, the sharp diffraction peak at 2θ=12.3° was observed which is due to the oxidation of graphite. The diffraction peak of pure graphite was found around 2θ=23.3°, corresponding to the highly organized layer structure with an interlayer distance along the (002) orientation. Clear and distinctive XRD peaks of ZnO were observed and shown in FIG. 2C. The peaks details are mentioned within the FIG. 2C itself. Interestingly, most of these peaks were also detected in ZnO incorporated rGO, except that GO peaks disappeared. Even in presence of gold, ZnO incorporated rGO samples showed those distinctive peaks without any hints for gold and GO. This phenomenon clearly indicates the evolution of ZnO nanostructures into different phases as observed directly in SEM imaging.

Figure 3A:
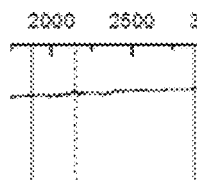
FIG. 3A shows FTIR spectra of pristine ZnO, rGO/ZnO and Au/rGO/ZnO nanostructures along with detailed peaks identification.

FTIR measurement was employed to understand further the presence of ZnO and ZnO incorporated rGO and rGO/gold as shown in FIG. 3A. The solid vertical (red) lines correspond to those peaks observed in GO samples whereas dotted vertical (black) lines correspond to those observed in ZnO samples. The details of the peaks definitions are mentioned therein. The intensities of the peaks are related to the amount of sample present. In case of ZnO incorporated rGO, a combination of the above-mentioned peaks with broad and low intensity was observed. In case of presence of gold, ZnO incorporated rGO showed almost no peak as observed from GO, except some distinctive peaks from ZnO. This is a further indication of the evolution of ZnO nanostructures into different phases.

Figure 3B:
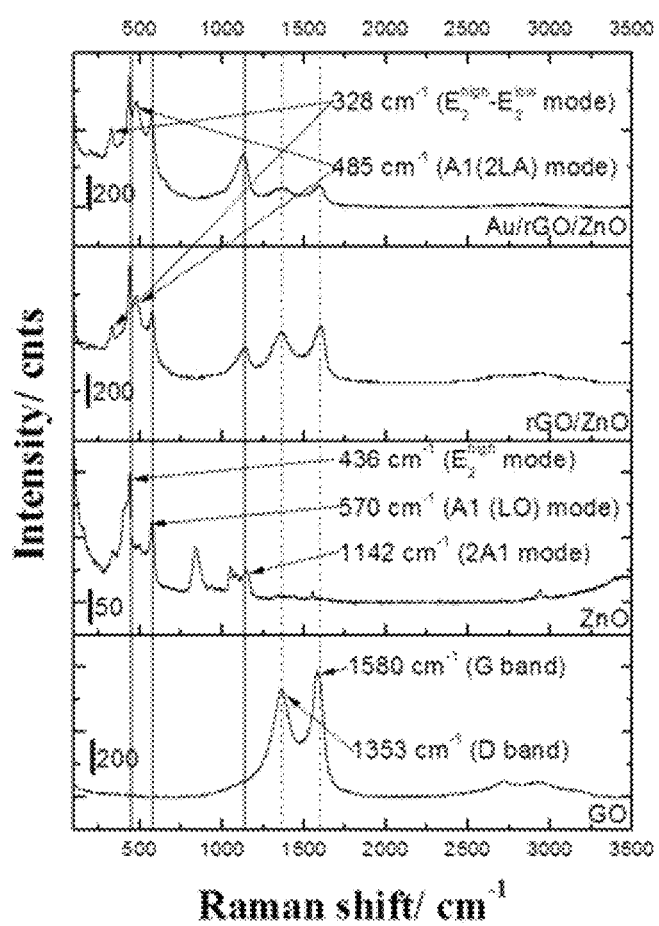
FIG. 3B shows Raman scattering spectra of pristine ZnO, rGO/ZnO, and Au/rGO/ZnO nanostructures along with detailed peaks identification.

Raman spectroscopy is very sensitive technique that can be used to investigate the presence of materials in various combinations as shown in FIG. 3B. The dotted vertical lines (red) represent Raman peaks of GO whereas solid black vertical lines correspond to those observed in ZnO. The details of the peaks are mentioned therein. The peaks obtained at ZnO incorporated rGO samples confirmed a combination of above-mentioned peaks as can be seen in FIG. 3B. Unlike those analysis done by XRD and FTIR, a clear indication of GO and ZnO Raman peaks were observed in presence of gold for ZnO incorporated rGO samples.

Figure 4A:
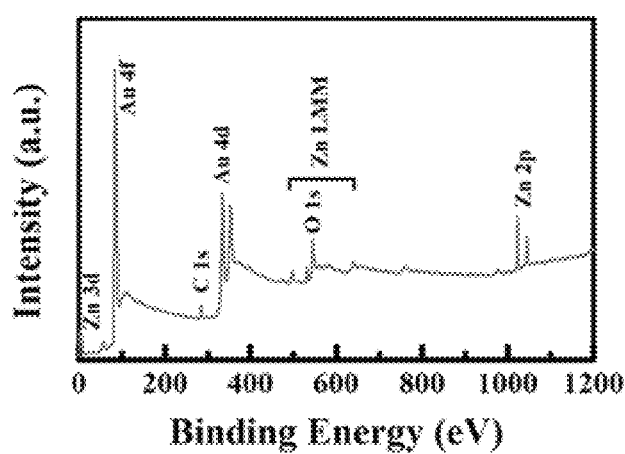
FIGS. 4A-4F illustrate the wide XPS survey spectrum for the Au/rGO/ZnO heterostructure.

The surface composition of the synthesized Au/rGO/ZnO heterostructure and the level of GO reduction were also examined by XPS analysis. FIG. 4A shows the XPS survey spectrum for the surface of the Au/rGO/ZnO heterostructure nanocomposite sensor, indicating the presence of the constituent elements (C, O, Zn and Au).

Figure 4B:
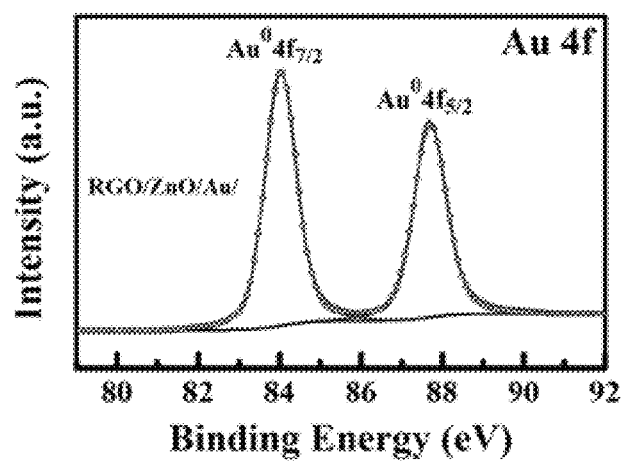
Figure 4C:
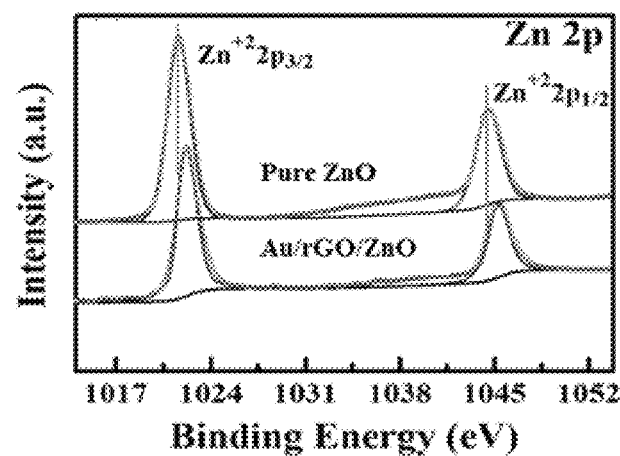

The Au 4f core level spectrum was split into two spin-orbit coupled doublets centered at binding energies of 84.0 eV and 87.7 eV assigned to Au $4f_{7/2}$ and Au $4f_{5/2}$ respectively, as shown in FIG. 4B. Similarly, both Zn 2p core level XPS spectra of the pure ZnO and Au/rGO/ZnO heterostructure nanocomposite sensor were split into two peaks (FIG. 4C), corresponding to the characteristic Zn $2p_{1/2}$ and Zn $2p_{3/2}$ signals and assigned to the $Zn^{+2}$ oxidation state. It can be observed that the binding energies of the two signals in pure ZnO are centered at 1021.7 and 1044.7 eV, respectively and were shifted to higher values of 1022.3 and 1045.3 eV, in the Au/rGO/ZnO heterostructure nanocomposite.

Interestingly, the positive shifts of 0.6 eV in Zn 2p peaks may be associated with the strong electronic interaction at the heterostructure interface due to the electron transfer from ZnO to Au nanoparticles.

Figure 4D:
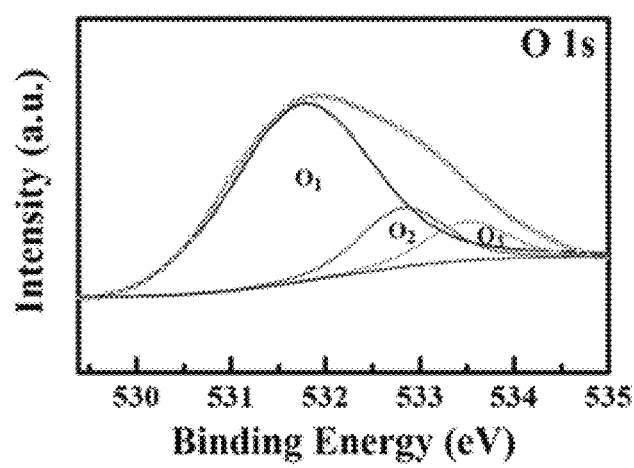

The 01 s core level spectrum of the Au/rGO/ZnO heterostructure nanocomposite sensor was also resolved into three individual segments designated as $O_1$, $O_2$, and $O_3$ at 531.76, 532.82 and 533.50 eV, respectively as shown in FIG. 4D. Segments $O_1$ and $O_2$ are indexed to Zn—O bonds in ZnO crystal lattice, and chemisorbed oxygen species on the ZnO surface, respectively. However, the third segment ($O_3$) is assigned to C—O band in rGO.

Figure 4E:
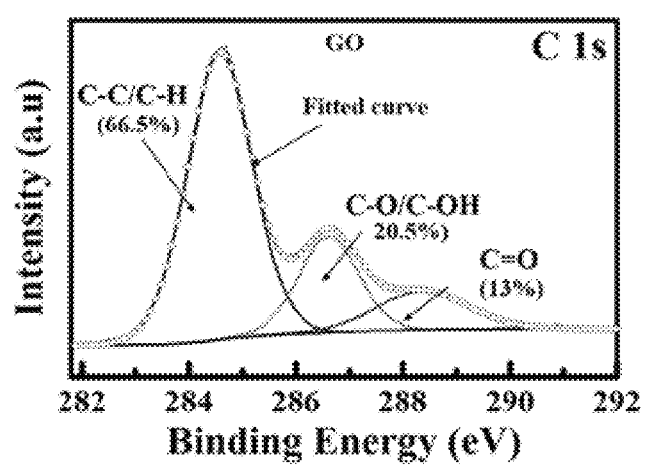

Finally, the C 1 s spectrum of GO was fitted (FIG. 4E) into three segments; C—C/C—H (284.5 eV), C—O/C—OH (286.6 eV), and C=O (288.3 eV), assigned to non-oxygenated $sp^2$ carbon representing the graphene structure, hydroxyl or epoxide and carbonyl functional groups, respectively.

Figure 4F:
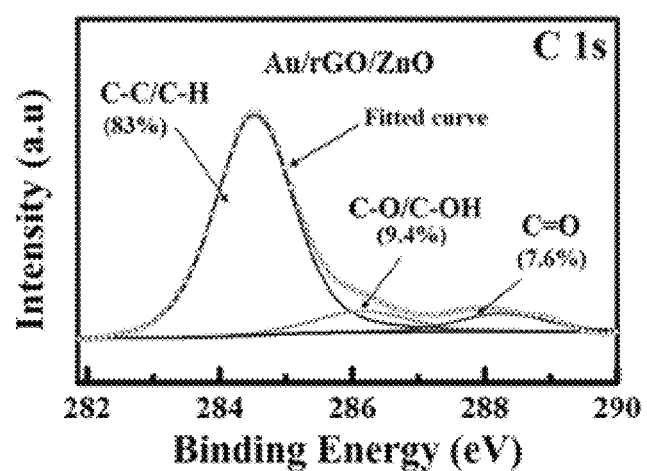

On the other hand, based on the XPS data, the total oxygen content in GO was 33.5% (C—O/C—OH: 20.5% and C=O: 13%), while the $sp^2$ carbon content was 66.5%. The reduction effect of laser ablation to GO was confirmed by fitting XPS spectrum of the Au/rGO/ZnO sample as shown in FIG. 4F.

After reduction, the total oxygen content in the Au/rGO/ZnO sample was reduced to 17%, while the $sp^2$ carbon content increased to 83%, revealing that a significant amount of oxygen functional groups was removed and the majority of the $sp^2$ carbon networks was retained. These observations confirm that a Au/rGO/ZnO heterostructure nanocomposite was successfully obtained.

Sensing Characteristics

FIG. 5 demonstrates the sensing response of the (a) ZnO nanorods, (b) rGO/ZnO heterostructure, and (c) Au/rGO/ZnO to 500 ppm $H_2$ at different operating temperatures with and without UV irradiation. As can be seen, the response of the ZnO sensor and rGO/ZnO sensors increased with operating temperature to reach a maximum value, and then decreased with further increases in temperature. The optimal operating temperature of ZnO nanorods appears at 250° C., while rGO/ZnO's optimal operating temperature is about 150° C. (FIGS. 5A and 5B)

It can be observed that the heterostructure not only reduces the operating temperature but also enhances the gas sensing response of the sensor. In detail, the sensing response of the ZnO nanorods toward 500 ppm $H_2$ at 250° C. is about 13% while rGO/ZnO's response at 150° C. is about 35%.

While not being bound to any particular theory, the observed characteristics can be ascribed to (1) the large surface area of the ZnO nanosheets and rGO, which in turn leads to increase the contact area between the adsorbed $H_2$ and rGO/ZnO nanocomposite, and (2) the Fermi level modulation due to the charges transfer at the interface of rGO and ZnO during the exposure and removal of $H_2$ gas.

In addition, the sensing response of the Au/rGO/ZnO sensor under thermal and UV activation were compared. Two main factors are competing to change the density of charge carriers in the heterostructure, which could enhance the sensing properties, i.e. photo-excitation using UV irradiation and thermal excitation using external heater.

Figure 5A:
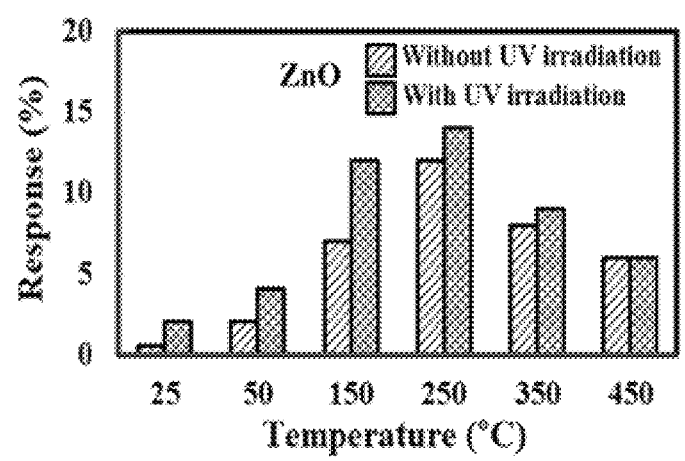
FIG. 5A shows the response of a pristine ZnO sensor with and without UV irradiation at different operating temperatures.
Figure 5B:
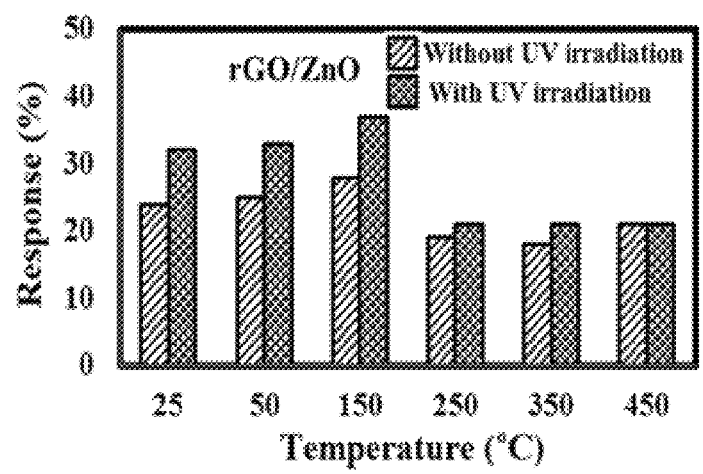
FIG. 5B response of a rGO/ZnO sensor with and without UV irradiation at different operating temperatures.
Figure 5C:
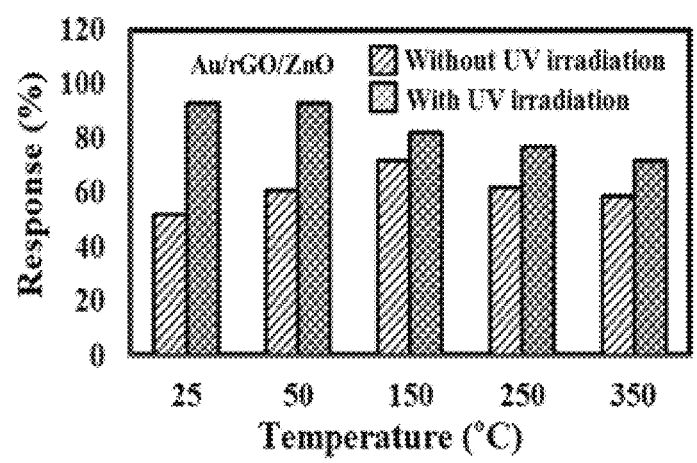
FIG. 5C response of a Au/rGO/ZnO sensor with and without UV irradiation at different operating temperatures.
Figure 5D:
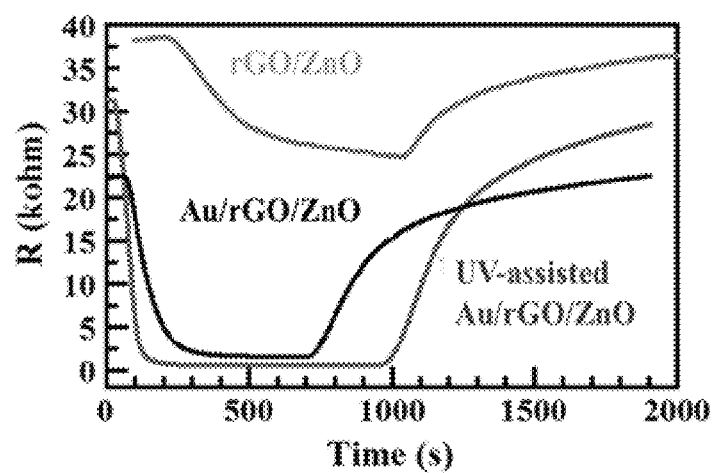
FIG. 5D shows the dynamic response of rGO/ZnO (top line), Au/rGO/ZnO (middle line), and UV activated Au/rGO/ZnO (lower line) sensors at room temperature (RT).

At low operating temperature (below 150° C.), both thermal and UV activation have positively contributed to improving the gas sensing properties of the ZnO and rGO/ZnO sensors. As the operating temperature increases, the significant difference in the sensing response decreases, indicating the predominant role of thermal activation. Interestingly, the operating temperature of the Au/rGO/ZnO sensor under UV illumination is shifted towards RT and exhibited superior $H_2$ sensing properties compared with the that of other sensors as seen in FIG. 5C. Furthermore, one can see from FIG. 5D that the Au/rGO/ZnO sensor in dark showed lower initial resistance than that of rGO/ZnO sensor and higher response at RT. On the other hand, the base resistance of the Au/rGO/ZnO under UV irradiation is higher and higher response is obtained which could be attributed to charges transfer in the composite.

Figure 6A:
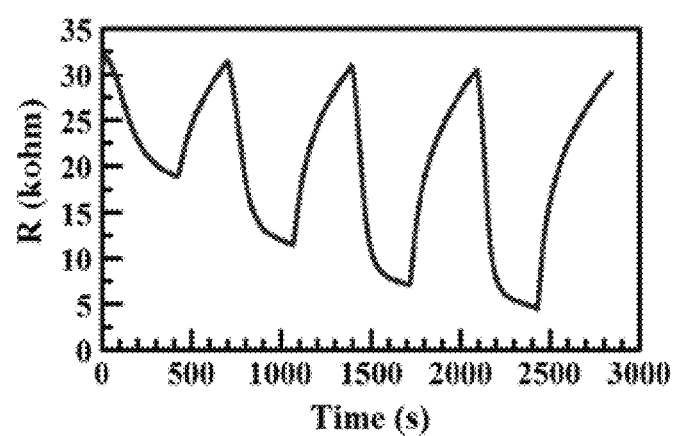
FIG. 6A illustrates a dynamic response curve of different hydrogen concentrations under UV irradiation at RT.

FIG. 6A shows a typical dynamic response of the Au/rGO/ZnO sensor against 30, 100, 300 and 500 ppm $H_2$ under UV irradiation at RT temperature. As can be observed, the sensor resistance values quickly decrease when the surface of the sensor is exposed to different levels of $H_2$ gas revealing the n-type semiconductor characteristic of the sensor.

In addition, the response amplitude of the fabricated sensors increases with increasing the $H_2$ concentration.

Figure 6B:
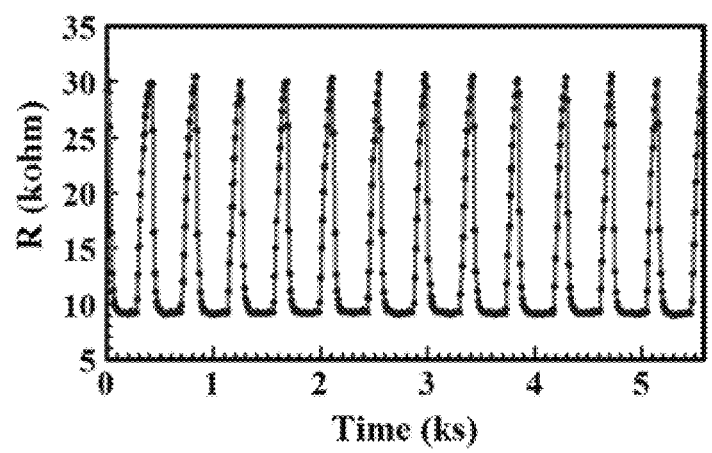
FIG. 6B describes repeatability measurements of the Au/rGO/ZnO sensor toward 300 ppm of $H_2$ at RT under UV illumination.

Repeatability is an important aspect that can be utilized to evaluate the reliability of the fabricated sensor. The repeatability of the Au/rGO/ZnO sensor was investigated via testing 500 ppm $H_2$ at RT under UV irradiation for consecutive thirteen cycles and the dynamic response curve is displayed in FIG. 6B. As can be noticed, there were no clear changes in sensor response during the repeated exposure and recovery cycles, revealing that the developed sensor maintains its initial response amplitude without a significant decrease.

Figure 6C:
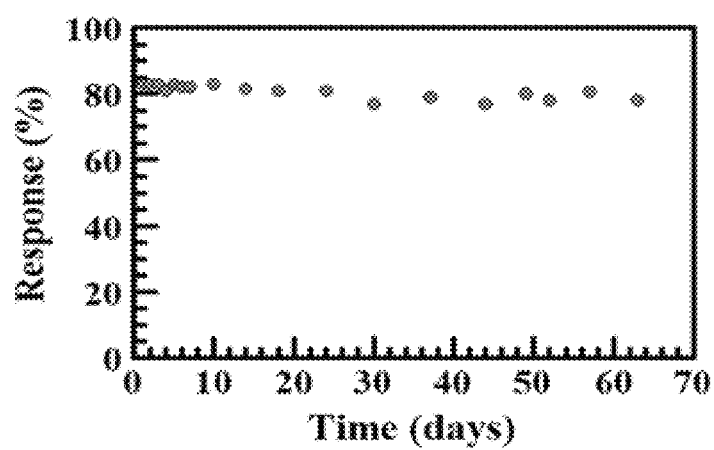
FIG. 6C depicts the long term stability of Au/rGO/ZnO sensor toward 500 ppm of $H_2$ under UV irradiation at RT.
Figure 6D:
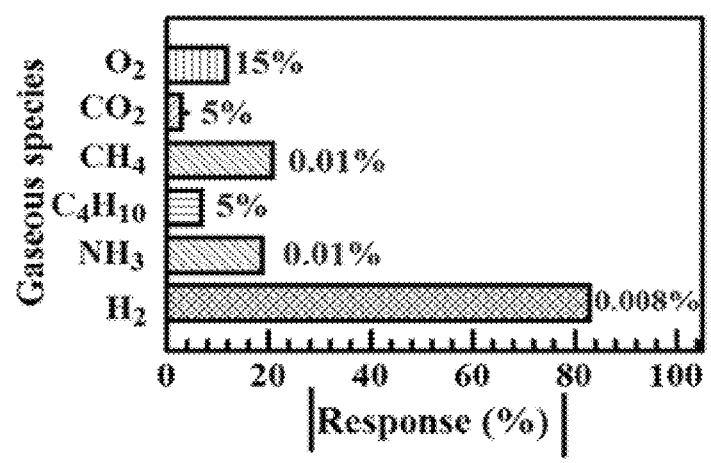
FIG. 6D shows selectivity test results for a Au/rGO/ZnO sensor toward 500 ppm of $H_2$ under UV irradiation at RT compared to other gases.

The long-term stability of the Au/rGO/ZnO sensor operating under UV irradiation at RT has been measured and is displayed in FIG. 6C which showed that the sensor response towards 500 ppm $H_2$ was nearly constant for over 60 days, confirming that the fabricated $H_2$ sensor possessed significant stability.

To examine the selectivity properties of the Au loaded rGO/ZnO sensor operating under UV-irradiation, 500 ppm of $H_2$ gas was utilized for the evaluation of the said sensor through comparison its response at RT with other interfering gases, e.g., $NH_3$, $C_4H_{10}$, $CH_4$, $CO_2$, and $O_2$. As can be seen in FIG. 6D, the absolute response to 500 ppm $H_2$ is significantly higher than the response of 15% (150,000 ppm) $O_2$, 5% (50,000 ppm) $C_4H_{10}$, 0.01% (1000 ppm) (50,000 ppm) $CO_2$, 0.01% (1000 ppm) NH3, and 0.01% (1000 ppm) $CH_4$, which was more than 1875, 625, and 1.25 times higher than the concentration of $H_2$ gas. The excellent selectivity towards $H_2$ gas could be resulted from the weak adsorptions of other gases molecules on the surface of the sensor at RT.

TABLE 1

Comparison of invention with earlier reported $H_2$ sensors

| Material | Working temperature (°C.) | Concentration (ppm) | Response | Light | Response and recovery time(s) | Response formula | Ref. |
|---|---|---|---|---|---|---|---|
| ZnO/NiO | 200 | 10 | 60 | No | 5-100 | $(R_a/R_g)/R_a$ | J. Lee, et al., Nanomaterials 8 (2018) 902 doi:10.3390/nano8110902. |
| WO$_3$/ZnO | 200 | 5,000 | 12.6 | No | — | $R_a/R_g$ | S. Park, Materials Letters 234 (2019) 315-318. |
| Pt/TiO$_2$/rGO | 180 | 500 | 46 | No | 54/58 | $(R_a/R_g)/R_a$ | A. Esfandiar, et al., Int. J. Hydrogen Energy 7 (2012) 1-10. |
| Au/TiO$_2$ | 170 | 200 ppm | 40 | Yes | 6.9-14 | $(R_a/R_g)/R_a$ | Nikfarjam, et al. Sensors and Actuators B: Chemical, 21:146-156, 2015 |
| Pt/rGO/ZnO | 100 | 400 | 99 | No | 12-412 | $(R_a/R_g)/R_a$ | Q.A. Drmosh, et al., Applied surface Science 464 (2019) 616-626 |
| SnO2 | 50 | 100 ppm | 9.5 | Yes | — | $R_a/R_g$ | T. Li, et al., Materials Letters 15 (2015) 648-651. |
| Pd-W$_2$N on porous Si | RT | 100 | 35.2 | No | 24.38 | $(R_a/R_g)/R_a$ | R. Prakash, et al., Sensors and Actuators B: Chemical 277 (2018) 665-672 |
| Au/ZnO | RT | 10,000 | 37 | Yes | 4.24 | $(R_a/R_g)/R_a$ | M. Kumar, et al., Nanotechnology 28 (2017) 365502. |

Table 1 compares the $H_2$ gas sensing properties of some nanostructured materials published in recent years with the present work. Although, some of the fabricated sensors showed fast response and recovery times, unlike the Au/rGO/ZnO sensor disclosed herein, they were working at a high operating temperature. Other comparative sensors only could detect high concentrations of $H_2$.

Gas Sensing Mechanism

While not being bound to a theory, based on the results, the gas sensing mechanism of the Au/rGO/ZnO may be described as follows. ZnO is a well-known n-type semiconductor while rGO is a p-type semiconductor. When the fabricated sensor is exposed to air ambient, oxygen molecules quickly attract and adsorb on the surface of the Au/rGO/ZnO sensing material to form chemisorbed oxygen ions as displayed in the following equations:

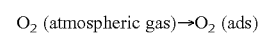
$O_2$ (atmospheric gas)→$O_2$ (ads)

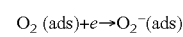
$O_2$ (ads)+$e$→$O_2^-$(ads)

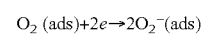
$O_2$ (ads)+$2e$→$2O_2^-$(ads)

Figure 7D:
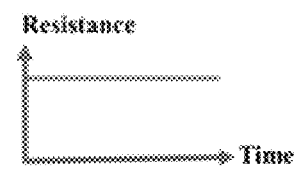
FIG. 7D shows resistance of sensor of FIG. 7C does not vary with exposure to air.
Figure 7E:
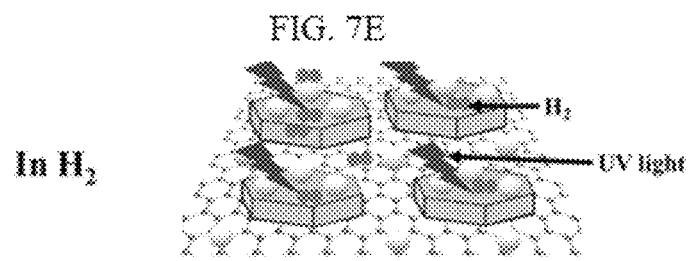
FIG. 7E illustrates gas sensing mechanism of Au/rGO/ZnO sensor when exposed in a $H_2$ environment with UV irradiation.
Figure 7F:
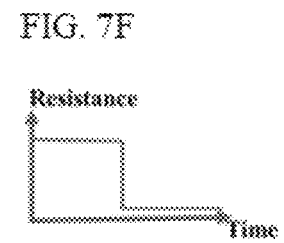
FIG. 7F shows decrease of resistance of sensor of FIG. 7E when $H_2$ is present.
Figure 8A:
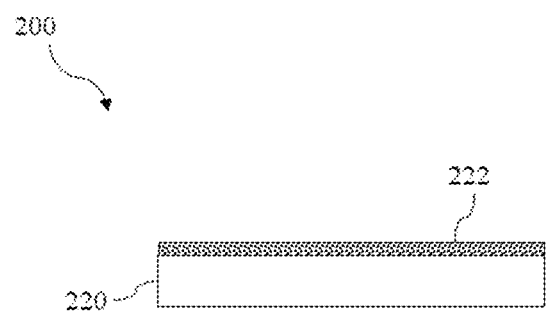
FIG. 8A schematically illustrates a side-view of a hydrogen gas sensor with a substrate and a Au/rGO/ZnO heterostructured thin film deposited thereon, wherein the zinc oxide heterostructured thin film covers an entire surface area of the substrate.
Figure 8B:
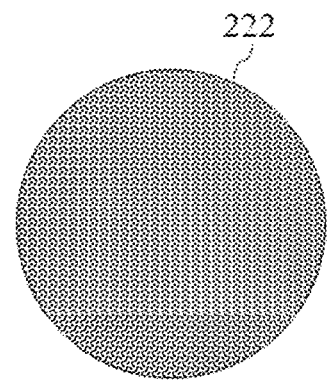
FIG. 8B schematically illustrates a top-view of a hydrogen gas sensor with a substrate and a Au/rGO/ZnO heterostructured thin film deposited thereon, wherein the zinc oxide heterostructured thin film covers an entire surface area of the substrate.
Figure 8C:
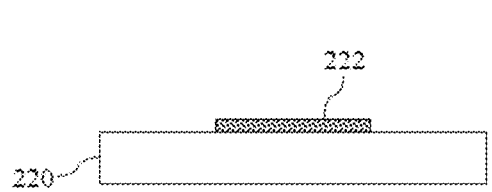
FIG. 8C schematically illustrates a side-view of a hydrogen gas sensor with a substrate and a Au/rGO/ZnO heterostructured thin film deposited thereon, wherein the zinc oxide heterostructured thin film covers a portion of the surface area of the substrate.
Figure 8D:
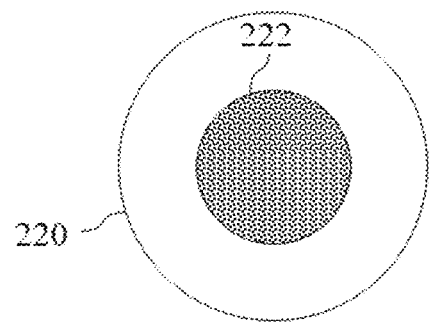
FIG. 8D schematically illustrates a top-view of a hydrogen gas sensor with a substrate and a Au/rGO/ZnO heterostructured thin film deposited thereon, wherein the zinc oxide heterostructured thin film covers a portion of the surface area of the substrate.

The density of carrier charge will decrease, which results in the construction of an electron depletion layer, increasing the electrical resistance of the sensor; FIGS. 7A-7B. Under UV irradiation, abundant electrons and holes were generated onto the surface of the sensor which in turn leads to extend the width of the depletion region causing the resistance to decrease further; FIGS. 7C-7D. When the surface of the Au/rGO/ZnO exposed to $H_2$ molecules, the $H_2$ molecules react with ionized oxygen species to form water and release the trapped electrons back to the bulk of the sensor leading to the decrease in the resistance of the sensor; FIGS. 7E-7F.

The improved $H_2$ sensing performance of the fabricated sensor could be attributed to several aspects: (i) unique high surface area of ZnO as confirmed by FESEM which provides abundant active sites for $H_2$ and $O_2$ molecules on the surface (ii) the formation of rGO/ZnO heterostructure as confirmed by Raman and FTIR is lowered the resistance of the sensor, thus making the sensor more active at lower temperature (iii) the work function difference between the Au ($q\varphi$=5.1 eV) and the ZnO ($q\chi$=4.09 eV) causing natural flow of free electrons from the ZnO to the surface of Au nanoparticles as confirmed by XPS. An additionally, The UV light enhancement of gas-sensing performance can be attributed to the reducing of activation energy between the surface of the sensor and $H_2$ gas.

As disclosed and exemplified herein, the inventors have developed a superior material useful for room temperature detection of hydrogen gas. This material is an Au decorated rGO/ZnO heterostructures which functions as a highly sensitive and efficient UV-activated $H_2$ gas sensor at room temperature. The physical structure of this material is described by FESEM micrography and its physical and chemical properties have been described by both optical and structural methods. Its $H_2$ sensing properties were demonstrated at room temperature under UV irradiation and compared to those of control materials ZnO and rGO/ZnO. As shown by FIGS. 5A-5D the responses of the Au decorated rGO/ZnO material at room temperature were significantly better than the control materials with or without UV irradiation. Moreover, the long term stability of the Au decorated rGO/ZnO material disclosed herein was demonstrated.

The invention claimed is:

1. A heterostructured composite comprising reduced graphene oxide (rGO) and flat hexagonal sheets of zinc oxide (ZnO) decorated with gold nanoparticles or with a thin gold film, wherein a weight ratio of rGO:ZnO ranges from 1.2:1 to 1:1.2.

2. The heterostructured composite of claim 1, wherein the flat hexagonal sheets of ZnO have a diameter ranging from 500-900 nm, a length on each side of about 250 to 500 nm and a thickness ranging from 25 to 100 nm.

3. The heterostructured composite of claim 1, wherein the flat hexagonal sheets of ZnO have a diameter of about 680-752 nm, a length on each side of about 357-395 nm and a thickness of 59 to 65 nm.

4. The heterostructured composite of claim 1 which is in the form of a sheet comprising a sheet of rGO attached to the flat hexagonal sheets of ZnO decorated with the Au nanoparticles or thin Au film.

5. The heterostructured composite of claim 1, wherein a weight ratio of rGO:ZnO is about 1:1.

6. The heterostructured composite of claim 1, wherein the flat hexagonal sheets of ZnO are decorated with gold nanoparticles and the gold nanoparticles comprise about 0.1 to 5 wt % of the heterostructured composite.

7. The heterostructured composite of claim 6, wherein the gold nanoparticles have an average diameter of 50 nm or less.

8. A hydrogen sensor comprising the heterostructured composite of claim 1, a substrate to which the heterostructured composite is bound, and electrodes, wherein the hydrogen sensor is configured to measure resistance, conductance, impedance or capacitance of the heterostructured composite.

9. The hydrogen sensor of claim 8, wherein the electrodes are interdigitated electrodes (IDE).

10. A method of detecting and/or quantifying hydrogen gas in a sample comprising:
contacting the hydrogen sensor of claim 8 with the sample,
measuring a decrease in one or more of resistance, conductance, impedance, or capacitance of the heterostructured composite occurring when the hydrogen sensor is in contact with the sample.

11. The method of claim 10, further comprising:
irradiating the hydrogen sensor with UV light during said contacting.

12. The method of claim 10, wherein the sample is a gas.

13. The method of claim 10 wherein the sample is a liquid.

14. The method of claim 10, wherein said contacting occurs at a temperature not exceeding 100° C.

15. The method of claim 10, wherein the hydrogen sensor is capable of detecting at least 500 ppm of hydrogen at room temperature (25° C.), wherein a relative difference between a first hydrogen concentration measurement and a second hydrogen concentration measurement is less than 1% or which has a repeatability of at least 99%.

16. A method for making the heterostructured composite of claim 1 comprising preparing ZnO nanorods by a hydrothermal method,
irradiating a mixture of graphene oxide (GO) and ZnO nanorods submerged in an aqueous medium with a UV laser for a time and under condition sufficient to reduce the GO to reduced graphene oxide (rGO) sheets, to exfoliate the ZnO nanorods, and to anchor the ZnO nanorods on the rGO sheets to form a heterostructured ZnO/rGO composite, and
depositing gold nanoparticles or a thin layer of Au on the heterostructured ZnO/rGO composite.

17. The method of claim 16, wherein said hydrothermal method used to produce the ZnO nanorods comprises heating an aqueous ethanolic solution of zinc nitrate, sodium hydroxide, and diethylamine at pH in the range of 11-14 and filtering and drying the resulting ZnO nano-rods,
wherein said UV laser used to irradiate the mixture of GO and ZnO has a wavelength of about 355 nm, and
wherein said depositing a thin layer of Au on a sheet of ZnO/rGO composite is performed by magnetron sputtering.

18. A method of detecting and/or quantifying hydrogen gas in a sample comprising:
contacting with the sample a hydrogen sensor comprising:
a heterostructured composite comprising reduced graphene oxide (rGO) and flat hexagonal sheets of zinc oxide (ZnO) decorated with gold nanoparticles or with a thin gold film, having a weight ratio of rGO:ZnO in a range of from 1.2:1 to 1:1.2;
a substrate to which the heterostructured composite is bound; and
electrodes, and
measuring a decrease in one or more of resistance, conductance, impedance, or capacitance of the heterostructured composite occurring when the hydrogen sensor is in contact with the sample,
wherein the hydrogen sensor is capable of detecting at least 500 ppm of hydrogen in the sample at room temperature.

* * * * *